United States Patent [19]
Schltt

[11] Patent Number: 5,992,214
[45] Date of Patent: Nov. 30, 1999

[54] METHOD AND DEVICE FOR ANALYZING VOLATILE SUBSTANCES IN GASES

[75] Inventor: Helmut Schltt, Cittiglio, Italy

[73] Assignee: European Atomic Energy Community (EURATOM), Luxembourg

[21] Appl. No.: 09/051,659

[22] PCT Filed: Oct. 24, 1996

[86] PCT No.: PCT/EP96/04624

§ 371 Date: Apr. 9, 1998

§ 102(e) Date: Apr. 9, 1998

[87] PCT Pub. No.: WO97/16723

PCT Pub. Date: May 9, 1997

[30] Foreign Application Priority Data

Oct. 30, 1995 [LU] Luxembourg ............................. 88675

[51] Int. Cl.⁶ .......................... G01N 01/14; G01N 31/08; G01N 30/00
[52] U.S. Cl. ................. 73/23.35; 73/23.42; 73/61.55; 73/864.86; 422/89; 435/296.1
[58] Field of Search ............... 73/23.35, 23.41, 73/23.42, 864, 86, 864.87, 61.52, 61.55, 61.59, 864.01; 422/88, 89; 435/296.1

[56] References Cited

U.S. PATENT DOCUMENTS

| | | | |
|---|---|---|---|
| 1,121,532 | 12/1914 | Newberry | 73/864.73 |
| 2,980,523 | 4/1961 | Dille et al. | 48/215 |
| 3,501,964 | 3/1970 | Drummond et al. | 73/425.6 |
| 3,604,269 | 9/1971 | Smith | 73/422 GC |
| 3,754,443 | 8/1973 | Harris, Sr. et al. | 73/422 GC |
| 3,824,859 | 7/1974 | Harris, Sr. et al. | 73/422 GC |
| 4,414,857 | 11/1983 | Brazhnikov et al. | 73/863.11 |
| 4,896,545 | 1/1990 | Averette | 73/863.01 |
| 5,012,845 | 5/1991 | Averette | 141/329 |
| 5,297,433 | 3/1994 | Elgas | 73/864.85 |
| 5,363,707 | 11/1994 | Augenblick et al. | 73/864.84 |
| 5,400,666 | 3/1995 | Song | 73/864.21 |
| 5,558,842 | 9/1996 | Vassiliou et al. | 422/108 |
| 5,646,336 | 7/1997 | Thompson et al. | 73/61.43 |
| 5,783,742 | 7/1998 | Shibamoto et al. | 73/23.41 |
| 5,801,282 | 9/1998 | Dassel et al. | 562/413 |
| 5,846,829 | 12/1998 | Worden et al. | 435/420 |

OTHER PUBLICATIONS

Gromping, et al., "Development of an Automated, Quasi-Continuous Method for the Simultaneous Determination of Nitrogen oxides, Aldehydes, and Ketones in Air", *Instrumentation Science & Technology*, vol. 22, No. 1, Feb. 1994, pp. 25–38.

H. Frank et al., "Quantitative Gas Chromatography Using a New Automated Derivatizer," *Journal of High Resolution Chromatography & Chromatography Communications*, vol. 8, Aug. 1985, No. 8, pp.411–414.

Gabriele, "Automation of Dissolution and Injection in HPLC Testing of Lyophilized Drugs," *International Laboratory*, vol. 21, Apr. 1991, No. 3, pp.38–41.

*Primary Examiner*—Hezron Williams
*Assistant Examiner*—J. David Wiggins
*Attorney, Agent, or Firm*—Sughrue, Mion, Zinn, Macpeak & Seas, PLLC

[57] ABSTRACT

The invention concerns a method and device for the automatic analysis of volatile substances in gases, in particular volatile substances in air, the method comprising the following successive steps: a) the gas to be analyzed is passed through an absortion solution or reaction solution via a sponging type exposure; and b) the solution is analyzed by a gas or liquid chromatography apparatus once the gases reach dissolved solution equilibrium with such absortion solution or reaction solution. According to the invention, samples as tiny as 10–100 microliters of the absortion solution or reaction solution are located in a depression in the bottom of a reaction recipient vessel and, when it has been acted on by the gas to be analyzed thereby additionally forming a reaction product mixed therein, is removed with a cannula and taken for chemical analysis via capillary gas chromatography (CGC) or high performance liquid chromatography (HPLC) equipment means.

3 Claims, 1 Drawing Sheet

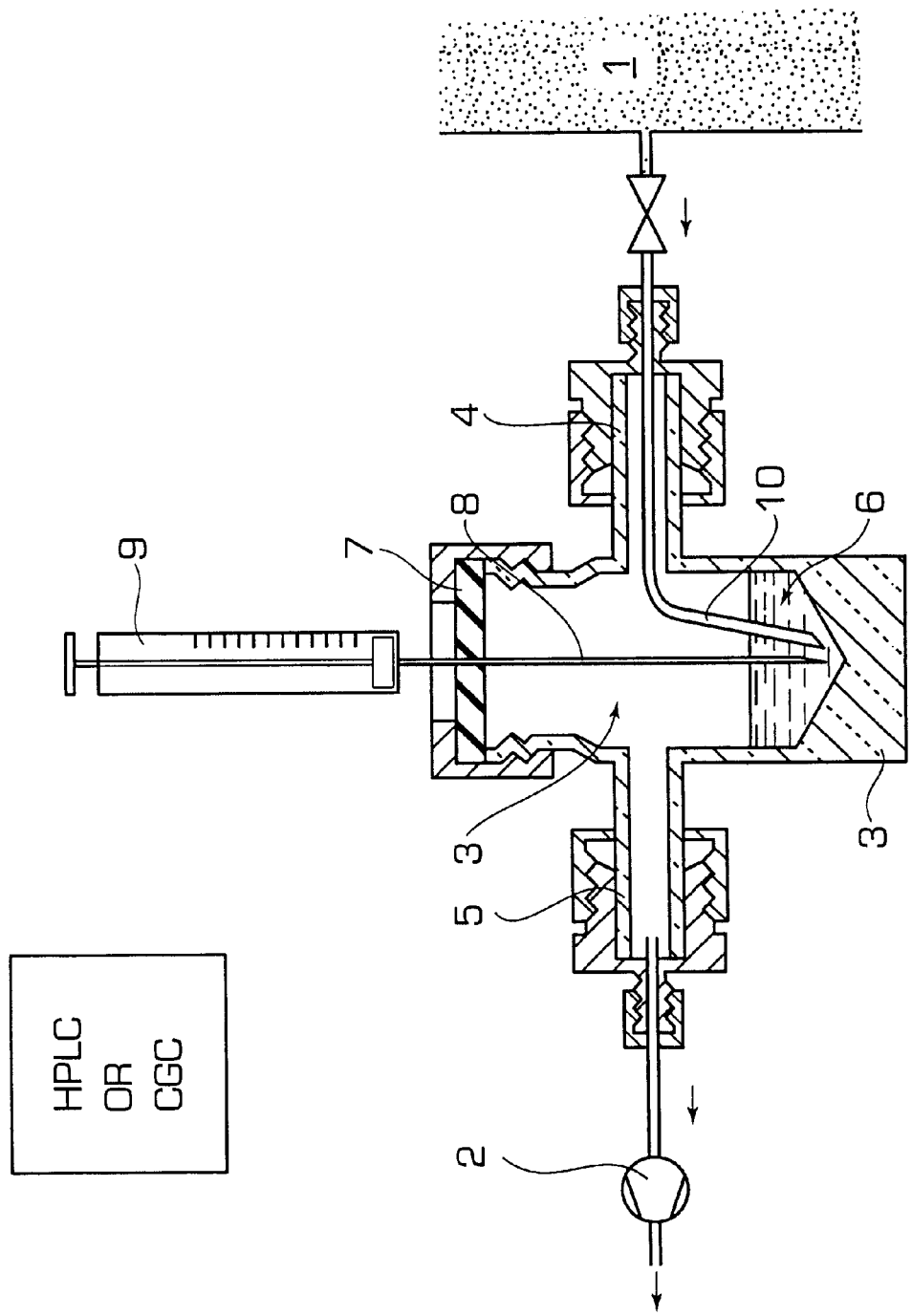

METHOD AND DEVICE FOR ANALYZING VOLATILE SUBSTANCES IN GASES

BACKGROUND OF THE INVENTION

The invention refers to a method and a device for automatically analyzing volatile substances in gases, in particular in air, the method comprising the following successive steps:

a) the gas to be analyzed is passed through an absorption or reaction solution, b) the solution is analyzed by a chromatography method.

Such methods and devices are known: An article of A. Grömping and K. Cammann "Development of an automated, quasi-continuous method for the simultaneous determination of nitrogen oxides, aldehydes, and ketones in air" published in the periodical INSTRUMENTATION SCIENCE & TECHNOLOGY 22 (1994), pages 25 to 38 describes a method of this type according to which the gas to be analyzed is passed through a recipient (impinger) which is nearly completely filled with a reaction solution, the gas sparkling upwards through the solution. After the intended exposure time a part of the solution is pumped via ducts and by means of a peristaltic pump into a chromatograph while the remaining solution is withdrawn from the recipient. The latter is then cleaned and charged with fresh solution for the next analysis cycle. All these steps are automatically supervised and controlled by a sequential program.

A main inconvenience of this method is the low sensitivity especially due to the following effects:

a) The analysis by means of the two chromatographic methods commonly in use, i.e. the high resolution liquid chromatography (HPLC) and the capillary gas chromatography (CGC) allows to inject only about 20 μl or 5 μl respectively of the absorption or reaction liquid into the chromatograph column. Taking into account a liquid volume of about 20 ml this represents only 1% or less of the entire sample volume and signifies a corresponding loss in sensitivity.

b) The absorption or reaction recipient having a volume of several milliliter cannot be cleaned at reasonable expenditure to an extent which is necessary for a sensitive measurement. Therefore the memory effect is high. The memory effect is further increased by the duct through which after exposure the solution to be analyzed must flow towards the chromatograph. For this reason this duct must also be cleaned after each analysis cycle. Moreover the volume of the recipient cannot be reduced in size at will since the length of this duct imposes a lower limit of recipient volume. Thus, in each cycle 20 ml of solution should be pumped towards the chromatograph. Under these conditions concentrations of down to 50 ppb of formaldehyde had to be measured.

The increasing pollution burden of closed rooms due to the improvements in the thermal isolation and the use of poisonous adhesives in the furniture industry and for posing wallpapers or carpets has created a need for a low cost measurement and supervision of even lower pollutant concentrations, especially the concentration of formaldehyde in the concentration range below 50 ppb.

SUMMARY OF THE INVENTION

It is therefore an object of the invention to propose a new method and a device adapted thereto allowing in a fully automatic manner the realisation of a sequence of analysis cycles which allows the extraction of a sample of gases to be analyzed, the adsorption of the sample in a reaction solution and finally the analysis of this solution and which permits measurement of very low concentration rates of pollutants, for example a formaldehyde concentration of 1 $\mu g/m^3$ or about 0.8 ppb. This object is achieved according to the invention by the method as defined in claim 1. The device for implementing this method is characterized by claim 3. Concerning features of a preferred embodiment of the method reference is made to claim 2.

The invention will now be described in more detail by means of a preferred embodiment and the attached drawings.

BRIEF DESCRIPTION OF THE DRAWINGS

The sole FIGURE is a sectional view a reaction recipient in which a reaction solution is submitted to the gas to be analyzed.

DESCRIPTION OF THE PREFERRED EMBODIMENT

The invention is explained in the frame of formaldehyde detection in ambient air, but it can also be applied to other products, especially pollutants in air or another support gas.

The air in a room 1 to be analyzed is sucked by means of a sucking pump 2 through a reaction recipient 3. The gas inlet 4 and the gas outlet 5 of this recipient are arranged in such a way that the gas to be analyzed is injected through a thin pipe 10 into an absorption and reaction solution which is located in a tiny depression 6 at the bottom of the recipient, such solution contained in a reaction recipient with said volatile substances and said gases reaching dissolved solution equilibrium with the absorption or reaction solution while a negative sucking pressure is applied to a headspace volume above the absorption or reaction solution. The inlet and the outlet can be disposed horizontally or along inclined lines in such a way that the pipe 10 extends rectilinearly towards the depression 6.

Above this depression the recipient is obturated by a septum 7 through which a cannula 8 can penetrate into the recipient. The recipient is for example made of a glass material which is inert with respect to the gas to be analyzed and to the reaction solution. The cannula is coupled to a transfer system 9 which has been shown here symbolically as a piston-type syringe but in reality the transfer system is automated and allows defined quantities of reaction products and cleaning liquids to be injected into the recipient or of exposed reaction liquid to be extracted therefrom in order to be transferred into an automated liquid chromatography column. The transfer system and the analysis column are known Per se and are for example commercialised under the designation SIL-7A by Shimadzu Corporation. In this commercial apparatus a plurality of test tubes each filled with an analysis sample are analyzed under the control of an automated sequence controller. A cannula penetrates through the septum of a tube, extracts a sample and transfers it into a liquid chromatography column in which the sample is analyzed separately by means of a convenient detector. After the cleaning of the cannula the next-following tube is treated.

The device according to the invention operates preferably as follows: At first the transfer system withdraws via the cannula 8 a certain quantity of cleaning liquid from a supply tank (not shown) and pours this liquid into the reaction recipient 3. By operating the sucking pump the cleaning liquid is distributed in the recipient in such a manner that the entire inner surface is rinsed. Thereafter the cleaning liquid is extracted through the cannula from the recipient and is discharged. The device is now ready to receive a well defined quantity of an acid solution of dinitrophenylhydrazine through the cannula 8. Thereafter the air or gas sample is applied. After the exposure which might last for seconds, minutes or hours, as the case may be, the admission of the air to be analyzed is interrupted. The next step is constituted by a complete withdrawal of the solution via the cannula 8 and by its transfer to a dosing system of a liquid chromatograph column allowing to measure the content in pollutants. This is the end of the cycle, and a new cycle begins. as explained above by cleaning the cannula and the reaction recipient, by filling in fresh reaction solution into the depression 6 and by again cleaning the cannula 8.

In the depression an extremely small reaction solution quantity of for example only 10 to 100 $\mu l$ can be charged which after the exposure is transferred totally through the cannula into the chromatograph. Due to this small quantity of solution which has become possible by the absence of the duct towards the chromatograph and by the direct transfer through the cannula, the pollutant concentration in the solution becomes higher and the cleaning of the recipient and the cannula is notably less complicated and consequently the memory effect is reduced to an extent that repeatable measurements of concentrations of for example formaldehyde in the range of 1 $\mu g/m^3$ or even below this value can be obtained.

Since the entire cycle is performed without human intervention, a large variety of analysis requirements can be fulfilled by an appropriate programming of the transfer system. This is true for example for the duration of the exposure and, as the case may be, for the waiting time between two successive sample extractions, as well as for the type and quantity of the reaction solution. Thus a complex and variable measurement program can be preprogrammed and is performed automatically without human intervention.

The device according to the invention can be realised by modifying the type SIL-7A injector mentioned above by simply withdrawing from the injector the rack intended to receive the plurality of test tubes and by mounting instead in a defined location the reaction recipient shown in the drawings. The transfer system then must only be guided to this location and to the tanks for the cleaning liquid and for the absorption or reaction solution or its components respectively instead of a plurality of test tubes awaiting in the rack successively their analysis. In the frame of the invention more than one reaction recipient 3 can be foreseen, especially two such recipients which are operated alternately, at each instant one of them being in the exposure phase and the other in the preparative phase for the next exposure. This allows a supervision of the air in a room or in the outer environment practically without interruption.

The invention is not restricted to the device shown in detail and to the corresponding method. Thus other pollutants than formaldehyde such as acetaldehyde, acrolein and acetone can be detected with the device according to the invention, and these pollutants can further be contained in other support gases than air. As the case may be, the reaction product can be a composition other than dinitrophenylhydrazine.

I claim:

1. A method for automatically analyzing volatile substances in gases, in particular air, comprising the following steps:

a) the gas to be analyzed via a sponging-type exposure is passed by bubbling upward through an absorption or reaction solution contained in a reaction recipient with said volatile substances and said gases reaching dissolved solution equilibrium with the absorption or reaction solution while a negative sucking pressure is applied to a head space volume above the absorption or reaction solution, as the case may be, b) the solution is analyzed by means of a chromatographic method, characterized in that 10 to 100 microliters of the absorption or reaction solution with a reaction product mixed therein is disposed in a depression of a reaction recipient and is completely extracted from the recipient through a cannula after the exposure to the gas to be analyzed by Capillary Gas Chromatograph (CGC) or High Performance Liquid Chromatograph (HPLC) techniques.

2. A method according to claim 1, characterized in that the reaction product in the solution is dinitrophenylhydrazine.

3. A device for automatically analyzing volatile substances in gases by the method according to claim 1, comprising:

a reaction recipient (3) present at the bottom of a depression (6) for the reaction solution and is obturated at the upper end and opposite to the depression by a septum (7) through which the cannula (8) is able to penetrate into the depression, in that the inlet into the recipient (3) for the gas to be analyzed terminates in a thin pipe (10) dipping into the depression whereas the outlet (5) connected to a sucking pump (2) is disposed laterally above the depression, and in that the cannula (8) is part of a automated transfer system know per se which under the control of a program automated sequence controlling injects a cleaning liquid into the recipient, discharges this liquid thereafter and injects a defined quantity of fresh solution of its components respectively into the reaction recipient for the next following analysis.

* * * * *